United States Patent
Kong et al.

(10) Patent No.: US 12,424,316 B2
(45) Date of Patent: Sep. 23, 2025

(54) CROSS-SESSION BRAINPRINT RECOGNITION METHOD BASED ON TENSORIZED SPATIAL-FREQUENCY ATTENTION NETWORK (TSFAN) WITH DOMAIN ADAPTATION

(71) Applicant: Hangzhou Dianzi University, Hangzhou (CN)

(72) Inventors: Wanzeng Kong, Hangzhou (CN); Xuanyu Jin, Hangzhou (CN); Xinyu Yang, Hangzhou (CN); Li Zhu, Hangzhou (CN); Jiajia Tang, Hangzhou (CN)

(73) Assignee: Hangzhou Dianzi University, Hangzhou (CN)

( * ) Notice: Subject to any disclaimer, the term of this patent is extended or adjusted under 35 U.S.C. 154(b) by 214 days.

(21) Appl. No.: 18/223,623

(22) Filed: Jul. 19, 2023

(65) Prior Publication Data
US 2024/0282439 A1    Aug. 22, 2024

(30) Foreign Application Priority Data
Feb. 17, 2023   (CN) ........................ 202310129985.7

(51) Int. Cl.
*G16H 40/63*     (2018.01)
*A61B 5/00*      (2006.01)
*A61B 5/31*      (2021.01)
*A61B 5/369*     (2021.01)
*G06N 20/00*     (2019.01)

(52) U.S. Cl.
CPC .............. *G16H 40/63* (2018.01); *A61B 5/31* (2021.01); *A61B 5/369* (2021.01); *A61B 5/7257* (2013.01); *G06N 20/00* (2019.01)

(58) Field of Classification Search
CPC ............................ G16H 40/60; G06N 20/00
See application file for complete search history.

(56) References Cited

U.S. PATENT DOCUMENTS

| | | | |
|---|---|---|---|
| 2019/0332751 A1* | 10/2019 | Brady | G06V 10/761 |
| 2020/0093392 A1* | 3/2020 | Tse | G16H 50/70 |
| 2023/0205133 A1* | 6/2023 | Matusik | G03H 1/04 |
| | | | 359/9 |
| 2023/0270369 A1* | 8/2023 | Trinkaus | A61B 5/381 |
| | | | 600/544 |

* cited by examiner

*Primary Examiner* — Jay M. Patel
(74) *Attorney, Agent, or Firm* — Thompson Hine LLP

(57) ABSTRACT

The present disclosure discloses a cross-session brainprint recognition method based on a tensorized spatial-frequency attention network (TSFAN) with domain adaptation. For most of existing multi-source domain adaptation methods, domain gaps between multiple source domains and target domains are individually bridged, but a relationship between domain-invariant features in distribution alignment is ignored. The present disclosure assists performance of a target domain by modeling an important relationship of the domain-invariant features without being affected by a distribution difference between source domains. A new TSFAN is used to combine pairwise source and target and an appropriate common spatial-frequency feature across source domains. Considering of a dimension, the TSFAN is further approximated as a low-rank Tucker format, to enable the TSFAN to adapt to scale linearly in a quantity of domains, and apply the TSFAN to a case of any quantity of sessions.

14 Claims, 2 Drawing Sheets

CROSS-SESSION BRAINPRINT RECOGNITION METHOD BASED ON TENSORIZED SPATIAL-FREQUENCY ATTENTION NETWORK (TSFAN) WITH DOMAIN ADAPTATION

CROSS REFERENCE TO RELATED APPLICATION

This patent application claims the benefit and priority of Chinese Patent Application No. 202310129985.7, filed with the China National Intellectual Property Administration on Feb. 17, 2023, the disclosure of which is incorporated by reference herein in its entirety as part of the present application.

TECHNICAL FIELD

The present disclosure pertains to the field of electroencephalogram (EEG) signal recognition in the field of biometric feature recognition, and specifically relates to a cross-session brainprint recognition method based on a tensorized spatial-frequency attention network (TSFAN) with domain adaptation. Specifically, a multi-source domain adaptation network based on tensorized spatial-frequency attention is introduced, and a transferable feature between pairwise source domain and target domain and interaction information between multiple domains are extracted, to mine a stable and reliable EEG identity feature for unsupervised classification.

BACKGROUND

Biometric recognition relies on an individual feature and plays a key role in an identity authentication system. Although physical biometric recognition, such as face recognition and fingerprint recognition, has been widely used in real life, a potential risk of elaborate forgery or surreptitious replication is still unavoidable. In addition to a physical biological feature, a brain activity recorded by an EEG signal is proposed as a new cognitive biological feature, which meets a basic identification requirement. In addition, signals of a brain activity can only be provided by a living individual, and these signals are not controlled by a user. This means that identity information of the user cannot be intentionally disclosed or stolen. Therefore, EEG-based biometrics is suitable for an application with a high security requirement.

A reliable and stable EEG identity feature is a basis for EEG-based biometric recognition. Actually, conventional machine learning methods are used in a large quantity of studies, in which expertise is particularly required to extract features, which are always insufficient to have good performance. In recent years, due to the ability of deep learning to capture high-level features and potential dependencies, deep learning has attracted considerable attention in decoding EEG recognition features. Generally, various types of deep learning methods, for example, a convolutional neural network (CNN), a recurrent neural network (RNN), and a graph convolutional neural network (GCNN), are proven to be capable of obtaining identity authentication features in temporal, frequency, and spatial from EEG signals.

EEG signals between different sessions are unstable due to factors such as impedance, a micro displacement of an electrode position, and a change of subject status. Thus, despite these significant advances, cross-session biometric recognition in a real-world scenario still faces challenges. In the past, most of the studies focus on data in a session or a mixed multi-session, but a distribution difference between EEG data in multiple training sessions is ignored. Intuitively, even in data between a single source domain (training session) and a single target domain (testing session), it is not easy to eliminate a domain invariant representing an extraction shift, and a larger degree of mismatch of multiple source domains may result in unsatisfactory performance.

To avoid the impact of a domain shift between multiple source domains, a multi-source domain adaptation method based on EEG signals is used to separately minimize differences between the source domains and target domains. Actually, a domain-invariant feature captured by using different source domains represents stable information from multiple views, and is used for transferring more appropriate information to the target domain. However, a domain-invariant feature calculated in each distribution alignment is affected by an involved source domain and cannot benefit from a common relationship of the multiple source domains.

In view of these problems, the present disclosure proposes a cross-session brainprint recognition method based on a TSFAN with domain adaptation to capture EEG identity features that are stable across sessions. Specifically, each pair of source domain data and target domain data is mapped to different time feature space. Then, a core idea of the TSFAN, namely, tensor-based attention, is designed, and a domain-invariant spatial-frequency feature is obtained by tensorizing spatial-frequency attention in the source domain and the target domain. These are naturally conducive to intra-source transferable information and complex inter-source interaction. Considering of a curse of dimensionality, a tensor in a low-rank Tucker format is further used, to enable the TSFAN to adapt to scale linearly in a quantity of domains.

SUMMARY

In view of the shortcomings of the conventional technology, the present disclosure aims to propose a cross-session brainprint recognition method based on a TSFAN with domain adaptation. The method is constructed mainly based on a TSFAN based on multi-source domain adaptation, and makes full use of an interaction correlation between different domains while pairwise alleviating a distribution difference between source domain data and target domain data.

A cross-session brainprint recognition method based on a TSFAN with domain adaptation includes the following steps:

step (1): preprocessing raw EEG data;

step 1-1: in a same experimental paradigm, acquiring EEG data generated by multiple subjects under external stimulation in different sessions;

step 1-2: after interference caused by factors such as an external device and electromyography (EMG) is eliminated, filtering the raw EEG data by using a Butterworth filter, and then performing Short-time Fourier Transform (STFT);

step 1-3: intercepting EEG data processed in step 1-2, and labeling corresponding EEG sample data with a label of a subject; and step 1-4: classifying EEG sample data processed in step 1-3 into a training set and a test set in proportion, where training set data includes data in K sessions, namely, K source domains, K≥2, and the test set serves as a target domain;

step (2): constructing a domain adaptation network model based on tensorized spatial-frequency attention, and training and testing the model, where the domain adaptation network model based on tensorized spatial-frequency attention includes K specific-domain feature extraction networks with a same structure and one TSFAN; each specific-domain feature extraction network includes a multi-scale one-dimensional convolutional layer, a concatenation layer, a maximum pooling layer, a fusion layer, and a spatial-frequency convolutional layer; the multi-scale one-dimensional convolutional layer includes multiple parallel one-dimensional convolutions at different scales; and the spatial-frequency convolutional layer includes a frequency-domain one-dimensional convolution and a spatial-domain one-dimensional convolution that are successively connected in series;

input of the multi-scale one-dimensional convolutional layer is one piece of source domain data and target domain data, which are output to the concatenation layer;

the concatenation layer concatenates received multiple features at different scales to obtain a source-domain brainprint temporal-domain feature $Zt_{sj}$ and a target-domain brainprint temporal-domain feature $Zt_{tj}$, where $j \in [1, K]$, and then separately outputs the foregoing features to the maximum pooling layer and the fusion layer;

the maximum pooling layer performs dimensionality reduction processing on the received features in a time dimension, and outputs processed features to the TSFAN;

the TSFAN receives features output by the maximum pooling layer of the K specific-domain feature extraction networks, performs interaction processing on the features to obtain source-domain spatial-frequency attention $Q_{sj}$ and target-domain spatial-frequency attention $Q_{tj}$ that include an interaction correlation between the features, and then outputs the foregoing attention to the fusion layer, specifically:

the TSFAN implements, by using two fully connected layers, nonlinear mapping of the features output by the K specific-domain feature extraction networks, to obtain the source-domain spatial-frequency attention $Q_{sj}$ and the target-domain spatial-frequency attention $Q_{tj}$:

$$Q_{sj} = F_{bj}(Relu(F_{aj}(P_{sj}; V_j)); U_j) \text{ and} \qquad \text{formula (1)}$$
$$Q_{tj} = F_{bj}(Relu(F_{aj}(P_{tj}; V_j)); U_j), \text{ where}$$

$F_{aj}$ and $F_{bj}$ represent two fully connected layers of $j^{th}$ source domain space, $V_j$ and $U_j$ represent parameters of the two fully connected layers, Relu(.) is an activation function, $P_{sj} \in \mathbb{R}^{c \times s}$ and $P_{tj} \in \mathbb{R}^{c \times s}$ represent a source-domain spatial-frequency feature and a target-domain spatial-frequency feature that are output by the maximum pooling layer, c is a quantity of EEG channels of a raw feature, and s is a frequency domain dimension size of the raw feature;

the fully connected layer parameter $U_j \in \mathbb{R}^{c's' \times cs}$ in formula (1) is tensorized to a (K+1)-order higher-order tensor $\mathbb{R}^{c's' \times c's' \times \ldots \times cs} \in \mathcal{W}$, to obtain the interaction correlation between the features, where c' is a quantity of EEG channels of a feature obtained after being processed by the fully connected layer $F_{aj}$, and s' is a frequency domain dimension size of the feature obtained after being processed by the fully connected layer $F_{aj}$, and considering that a curse of dimensionality is caused as a quantity of source domains increases, a low-rank Tucker form is used to represent the higher-order tensor $\mathcal{W}$:

$$\mathcal{W} = \mathcal{U} \times_1^2 W_1 \times_2^2 W_2 \times \ldots \times_{K+1}^2 W_{K+1}, \qquad \text{formula (2)}$$

where $$\mathcal{U} \in \mathbb{R}^{r_1 \times \ldots \times r_{K+1}}, \{W_n \in \mathbb{R}^{r_n \times I_n}\}_{n=1}^{K+1}, \{r_1 \ldots r_{K+1}\}$$

is ranks in the Tucker form, $I_1 = I_2 = \ldots = I_K = c's'$, $I_{K+1} = cs$, c is a quantity of EEG channels of a raw feature, and s is a frequency domain dimension size of the raw feature;

the fusion layer respectively fuses the received source-domain brainprint temporal-domain feature $Zt_{sj}$ and the received target-domain brainprint temporal-domain feature $Zt_{tj}$ with the source-domain spatial-frequency attention $Q_{sj}$ and the target-domain spatial-frequency attention $Q_{tj}$, to obtain a source-domain brainprint temporal-domain feature $Zt'_{sj}$ and a target-domain brainprint temporal-domain feature $Zt'_{tj}$ that are spatial-frequency enhanced, and outputs the obtained features to the spatial-frequency convolutional layer; and the spatial-frequency convolutional layer extracts the received temporal-domain features $Zt'_{sj}$ and $Zt'_{tj}$ by using a frequency-domain one-dimensional convolution operation and a spatial-domain one-dimensional convolution operation, to obtain a source-domain temporal-spatial-frequency brainprint feature $Z_{sj}$ and a target-domain temporal-spatial-frequency brainprint feature $Z_{tj}$;

step (3): constructing a classifier used for brainprint recognition, and training and testing the classifier; and flattening the temporal-spatial-frequency features $Z_{sj}$ and $Z_{tj}$ that are output in step 2, and calculating, by using the fully connected layer and a Softmax activation function, a probability that a sample belongs to each category; and step (4): implementing cross-session brainprint recognition by using the domain adaptation network model based on tensorized spatial-frequency attention and the classifier used for brainprint recognition that are trained and tested.

Preferably, the filtering the raw EEG data by using a Butterworth filter in step 1-2 is specifically: downsampling the EEG data to 250 Hz, and performing 0-75 Hz filtering processing on the raw EEG data by using the Butterworth filter.

Preferably, the performing FFT in step 1-2 is specifically: performing short-time Fourier transform (STFT) on a filtered signal x to extract a temporal-frequency feature, where
a time-limited window function h(t) is used, it is assumed that a non-stationary signal x is stationary in one time window, a group of local "spectra" of the signal are obtained by performing segment-by-segment analysis on the signal x by moving the window function h(t) on a time axis, and STFT of a signal x(τ) is defined as:

$$STFT(t, f) = \int_{-\infty}^{\infty} x(\tau)h(\tau - t)e^{-j2\pi f\tau}d\tau, \quad \text{formula (3)}$$

where

STFT(t,f) represents STFT of the signal x(τ) at time t, h(τ− t) is a window function, and f represents a frequency.

Preferably, the fusion layer is specifically:

$$Zt'_{sj} = Zt_{sj} + Zt_{sj} \otimes \text{Sigmoid}(Q_{sj}) \quad \text{formula (4)}$$

and $$Zt'_{tj} = Zt_{tj} + Zt_{tj} \otimes \text{Sigmoid}(Q_{tj})$$

Preferably, a loss function $\mathcal{L}_{cls}$ of the classifier used for brainprint recognition is:

$$\mathcal{L}_{cls} = E(\theta_f, \theta_y) = \sum_{i=1,\ldots,N} \mathcal{L}_y^i(\theta_f, \theta_y), \quad \text{formula (5)}$$

where $\theta_y$ is a classifier parameter, N is a quantity of categories, $\theta_f$ represents a feature extractor parameter $\mathcal{L}_y^i(\theta_f,\theta_y)$ represents a cross-entropy loss of an $i^{th}$ type, and E( ) represents a cross-entropy function.

Preferably, a total loss function $\mathcal{L}_{total}$ of the domain adaptation network model based on tensorized spatial-frequency attention and the classifier used for brainprint recognition is:

$$\mathcal{L}_{total} = \mathcal{L}_{cls} + \lambda \mathcal{L}_{dist} + \gamma \mathcal{L}_{disc}, \quad \text{formula (6)}$$

where $\mathcal{L}_{disc}$ represents a loss function used to measure the distance of the classifier, $\mathcal{L}_{dist}$ represents a loss function used to measure the distribution difference between the source domain data and the target domain data, and λ and γ are super parameters.

The present disclosure further aims to provide a cross-session brainprint recognition apparatus, including:
an EEG data preprocessing module, configured to perform filtering and FFT on acquired EEG data in different sessions;
a domain adaptation network model based on tensorized spatial-frequency attention that is trained and tested, configured to perform feature extraction on EEG data that is in the different sessions and that is output by the EEG data preprocessing module, to obtain a source-domain temporal-spatial-frequency brainprint feature $Z_{sj}$ and a target-domain temporal-spatial-frequency brainprint feature $Z_{tj}$; and
a classifier used for brainprint recognition that is trained and tested, configured to flat the source-domain temporal-spatial-frequency brainprint feature $Z_{sj}$ and the target-domain temporal-spatial-frequency brainprint feature $Z_{tj}$, and calculate, by using a fully connected layer and a Softmax activation function, a probability that a sample belongs to each category, to implement cross-session brainprint recognition.

The present disclosure further aims to provide a computer-readable storage medium, a computer program is stored on the computer-readable storage medium, and when the computer program is executed in a computer, the computer is enabled to perform the foregoing method.

The present disclosure further aims to provide a computing device, including a memory and a processor, the memory stores executable code, and when executing the executable code, the processor implements the foregoing method.

The present disclosure has the following beneficial effects:

The present disclosure proposes to combine capturing of intra-source transferable information of domain-invariant features with cross-source interaction, to alleviate a determining ability reduction due to global distribution alignment, and proposes a tensor-based attention mechanism that tensorizes attention in a specific field in a low-rank Tucker format, allowing the mechanism to interact between multiple source views without being affected by a curse of dimensionality. The method in the present disclosure is expected to be used as a brainprint recognition method to be applied to a scenario with high confidentiality.

DETAILED DESCRIPTION OF THE EMBODIMENTS

To make the objectives, technical solutions, and advantages of the present disclosure clearer, detailed descriptions are further provided below with reference to the technical solutions and accompanying drawings of the present disclosure.

Figure 1:
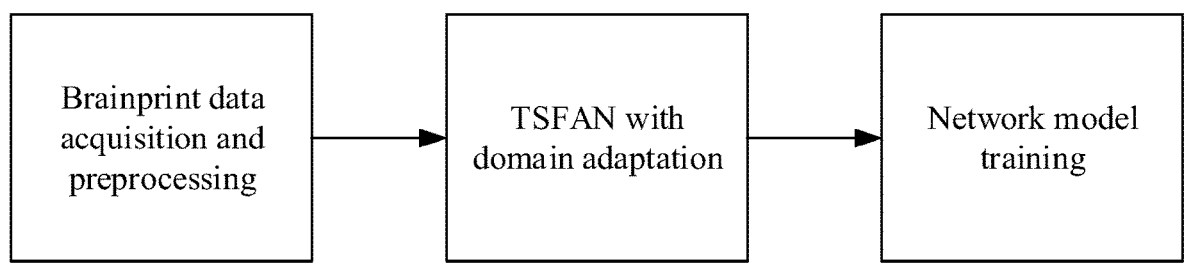
FIG. 1 is a flowchart of a brainprint recognition model according to the present disclosure.
Figure 2:
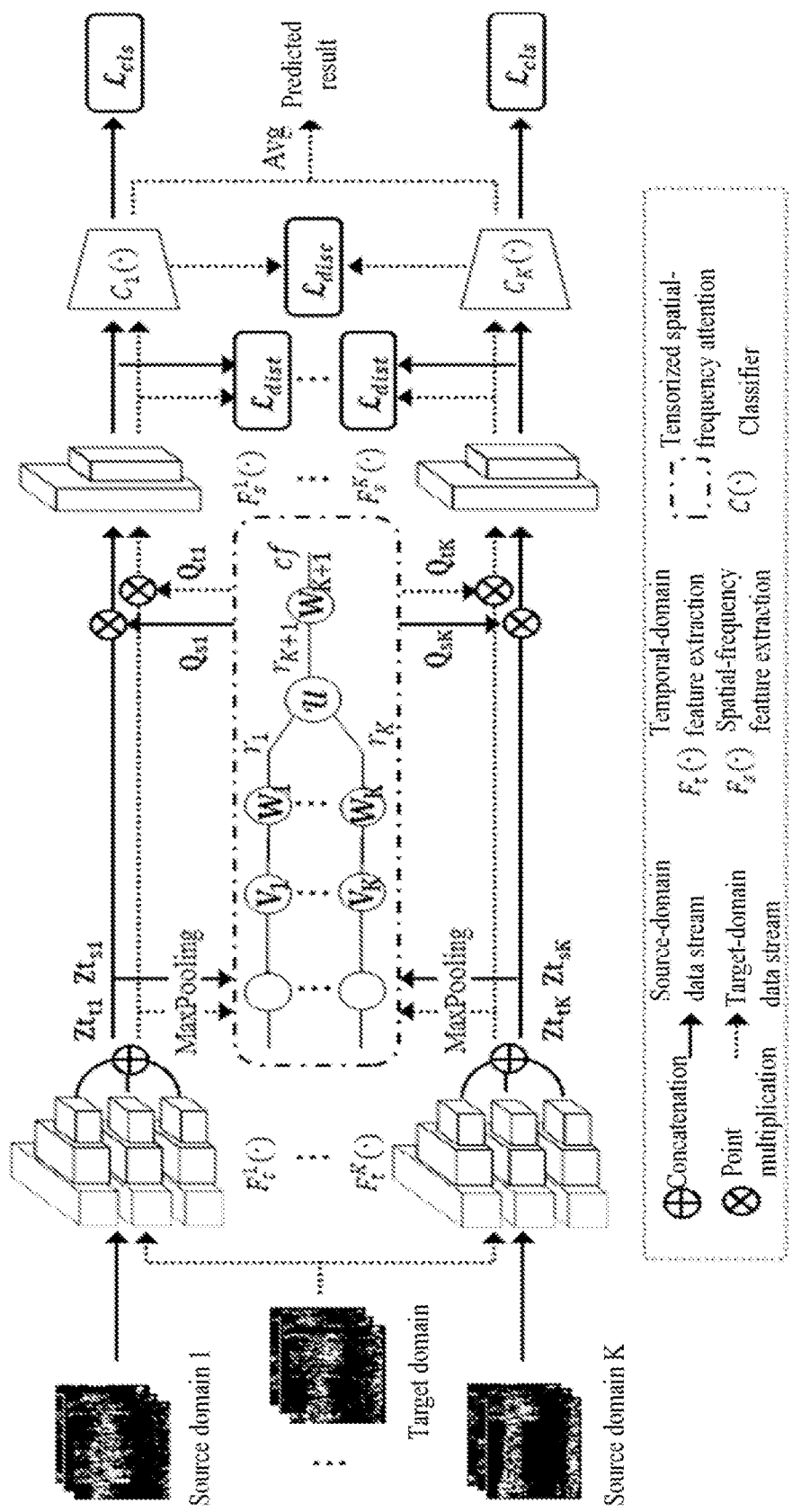
FIG. 2 is a diagram of an architecture of a domain adaptation network based on tensorized spatial-frequency attention according to the present disclosure.

The present disclosure relates to a cross-session brainprint recognition method based on a TSFAN with domain adaptation. A flowchart of the method is shown in FIG. 1. A model architecture diagram is shown in FIG. 2, and specifically includes two modules: (1) an intra-source transferable-feature learning module, configured to perform multi-source domain adaptation by using a time feature extractor and a spatial-frequency feature extractor, to obtain a domain-invariant feature of each pairwise source domain and target domain; and (2) a tensorized spatial-frequency attention module, configured to simulate complex inter-source interactions. The entire architecture is well designed to explore stable EEG recognition features across sessions.

Step 1: Preprocess Raw EEG Data.

(1) A frequency of a noise included in the raw EEG signal is usually lower than 0.5 Hz or higher than 50 Hz. To eliminate power-frequency interference caused by an EEG acquisition device and EMG interference of a subject, the EEG data is downsampled to 250 Hz, and 0-75 Hz filtering processing is performed on the raw EEG data by using a Butterworth filter.

(2) Perform STFT on a signal x output by step (1) to extract a temporal-frequency feature. A time-limited window function h(t) is used, it is assumed that a non-stationary signal x is stationary in one time window, a group of local "spectra" of the signal are obtained by performing segment-by-segment analysis on the signal x by moving the window function h(t) on a time axis. A specific size of the window in this solution is 0.5 s. STFT of a signal x(τ) is defined as:

$$STFT(t,\ f) = \int_{-\infty}^{\infty} x(\tau)h(\tau-t)e^{-j2\pi f\tau}d\tau,$$

where

STFT(t,f) represents STFT of the signal $x(\tau)$ at time t, $h(\tau- t)$ is a window function, and f represents a frequency.

(3) By using time windows of 15 s, intercept EEG data processed in step (2), and label corresponding EEG sample data with a label of a subject.

(4) Classify EEG sample data processed in step (3) into a training set $\{X_{sj},\ Y_{sj}\}_{j=1}^{K}$ and a test set $\{X_t,\ Y_t\}$ in proportion, where K is a quantity of sessions. An EEG sample $x \in \mathbb{R}^{c \times s \times t}$ where c is a quantity of EEG channels, s is a size of a frequency domain dimension, and t is a $\mathbb{R}^{c \times s \times t}$ size of a time domain dimension. In this solution, nine channels: Fz, F7, F8, C3, C4, P7, P8, O1, and O2 are selected, including 1-30 Hz and a sampling rate of 250 Hz, that is, c=9, s=30, and t=30.

Step 2: Construct a domain adaptation network model based on tensorized spatial-frequency attention, where the domain adaptation network model based on tensorized spatial-frequency attention includes K specific-domain feature extraction networks with a same structure and one TSFAN; each specific-domain feature extraction network includes a multi-scale one-dimensional convolutional layer, a concatenation layer, a maximum pooling layer, a fusion layer, and a spatial-frequency convolutional layer; the multi-scale one-dimensional convolutional layer includes multiple parallel one-dimensional convolutions at different scales; and the spatial-frequency convolutional layer includes a frequency-domain one-dimensional convolution and a spatial-domain one-dimensional convolution that are successively connected in series;

input of the multi-scale one-dimensional convolutional layer is one piece of source domain data and target domain data, which are output to the concatenation layer;

the concatenation layer concatenates received multiple features at different scales to obtain a source-domain brainprint temporal-domain feature $Zt_{sj}$ and a target-domain brainprint temporal-domain feature $Zt_{tj}$, where $j \in [1,\ K]$, and then separately outputs the foregoing features to the maximum pooling layer and the fusion layer;

the maximum pooling layer performs dimensionality reduction processing on the received features in a time dimension, and outputs processed features to the TSFAN;

the TSFAN receives features output by the maximum pooling layer of the K specific-domain feature extraction networks, performs interaction processing on the features to obtain source-domain spatial-frequency attention $Q_{sj}$ and target-domain spatial-frequency attention $Q_{tj}$ that include an interaction correlation between the features, and then outputs the foregoing attention to the fusion layer, specifically:

the TSFAN implements, by using two fully connected layers, nonlinear mapping of the features output by the K specific-domain feature extraction networks, to obtain the source-domain spatial-frequency attention $Q_{sj}$ and the target-domain spatial-frequency attention $Q_{tj}$:

$$Q_{sj} = F_{bj}(Relu(F_{aj}(P_{sj};\ V_j));\ U_j) \quad \text{formula (1)}$$

and $$Q_{tj} = F_{bj}(Relu(F_{aj}(P_{tj};\ V_j));\ U_j),$$

$F_{aj}$ and $F_{bj}$ represent two fully connected layers of $j^{th}$ source domain space, $V_j$ and $U_j$ represent parameters of the two fully connected layers, Relu(.) is an activation function, $P_{sj} \in \mathbb{R}^{c \times s}$ and $P_{tj} \in \mathbb{R}^{c \times s}$ represent a source-domain spatial-frequency feature and a target-domain spatial-frequency feature that are output by the maximum pooling layer, c is a quantity of EEG channels of a raw feature, and s is a frequency domain dimension size of the raw feature;

the fully connected layer parameter $U_j \in \mathbb{R}^{c's' \times cs}$ in formula (1) is tensorized to a (K+1)-order higher-order tensor $\mathcal{W} \in \mathbb{R}^{c's' \times c's' \times \ldots \times cs}$, to obtain the interaction correlation between the features, where c' is a quantity of EEG channels of a feature obtained after being processed by the fully connected layer $F_{aj}$, and s' is a frequency domain dimension size of the feature obtained after being processed by the fully connected layer $F_{aj}$, and considering that a curse of dimensionality is caused as a quantity of source domains increases, a low-rank Tucker form is used to represent the higher-order tensor $\mathcal{W}$:

$$\mathcal{W} = \mathcal{U} \times_1^2 W_1 \times_2^2 W_2 \times \ldots \times_{K+1}^2 W_{K+1}, \quad \text{formula (2)}$$

where $$\mathcal{U} \in \mathbb{R}^{r_1 \times \ldots \times r_{K+1}},\ \{W_n \in \mathbb{R}^{r_n \times I_n}\}_{n=1}^{K+1},\ \{r_1 \ldots r_{K+1}\}$$

is ranks in the Tucker form, $I_1\ I_2 = \ldots = I_K = c's'$, $I_{K+1} = cs$, c is a quantity of EEG channels of a raw feature, and s is a frequency domain dimension size of the raw feature; and the fusion layer respectively fuses the received source-domain brainprint temporal-domain feature $Zt_{sj}$ and the received target-domain brainprint temporal-domain feature $Zt_{tj}$ with the source-domain spatial-frequency attention $Q_{sj}$ and the target-domain spatial-frequency attention $Q_{tj}$, to obtain a source-domain brainprint temporal-domain feature $Zt'_{sj}$ and a target-domain brainprint temporal-domain feature $Zt'_{tj}$ that are spatial-frequency enhanced, and outputs the obtained features to the spatial-frequency convolutional layer, specifically:

$$Zt'_{sj} = Zt_{sj} + Zt_{sj} \otimes \text{Sigmoid}(Q_{sj}) \quad \text{formula (4)}$$

and $$Zt'_{tj} = Zt_{tj} + Zt_{tj} \otimes \text{Sigmoid}(Q_{tj})$$

where the spatial-frequency convolutional layer extracts the received temporal-domain features $Zt'_{sj}$ and $Zt'_{tj}$ by using a frequency-domain one-dimensional convolution operation and a spatial-domain one-dimensional convolution operation, to obtain a source-domain temporal-spatial-frequency brainprint feature $Z_{sj}$ and a target-domain temporal-spatial-frequency brainprint feature $Z_{tj}$.

Step 3: Construct a classifier used for brain brainprint recognition; and flatten the temporal-spatial-frequency features output in step 2, and calculate, by using the fully connected layer and a Softmax activation function, a probability that a sample belongs to each category. A loss function of the classifier is defined as:

$$\mathcal{L}_{cls} = E(\theta_f, \theta_y) = \sum_{k=1,\ldots,N} \mathcal{L}_y^i(\theta_f, \theta_y), \quad \text{formula (5)}$$

where $\theta_y$ is a classifier parameter, and N is a quantity of categories.

Step 4: Train the network model.

Gradient back propagation is performed, by using the training set obtained in (4) of step 1, on the model constructed in step 2 to step 3 to optimize the loss function, and a validation set obtained in (4) of step 1 is saved as a best model for testing. The loss function is expressed as follows:

$$\mathcal{L}_{total} = \mathcal{L}_{cls} + \lambda \mathcal{L}_{dist} + \gamma \mathcal{L}_{disc}, \quad \text{formula (6)}$$

where $\mathcal{L}_{disc}$ is used to measure a distance of the classifier, $\mathcal{L}_{dist}$ is used to measure a distribution difference between the source domain data and the target domain data, and $\lambda$ and $\gamma$ are super parameters, which are set to 0.5 in the present disclosure. A stochastic gradient descent (SGD) optimizer is used, a learning rate is 0.025, and batch-_size is 64.

Step 5: Verify validity of this solution on a multi-task identification data set, including 30 subjects, that is, N=30. Data in a first session and data in a last session are reserved to test two data classification manners for verification. A comparison experiment is performed on existing methods of domain consolidation and multiple source domains, and a result is shown in Table 1. The verification result shows that the model proposed in the present disclosure can effectively extract stable brainprint features in different sessions.

What is claimed is:

1. A method for cross-session brainprint recognition based on a tensorized spatial-frequency attention network (TSFAN) with domain adaptation, comprising the following steps:

step (1): preprocessing raw electroencephalogram (EEG) data;

step 1-1: in a same experimental paradigm, acquiring EEG data generated by multiple subjects under external stimulation in different sessions;

step 1-2: filtering the raw EEG data by using a Butterworth filter, and then performing Short-time Fourier Transform (STFT);

step 1-3: intercepting EEG data processed in step 1-2, and labeling corresponding EEG sample data with a label of a subject; and step 1-4: classifying EEG sample data processed in step 1-3 into a training set and a test set in proportion, wherein training set data comprises data in K sessions, namely, K source domains, K≥2, and the test set serves as a target domain;

step (2): constructing a domain adaptation network model based on tensorized spatial-frequency attention, and training and testing the domain adaptation network model based on tensorized spatial-frequency attention wherein the domain adaptation network model based on tensorized spatial-frequency attention-comprises K specific-domain feature extraction networks with a same structure and one TSFAN; each specific-domain feature extraction network comprises a multi-scale one-dimensional convolutional layer, a concatenation layer, a maximum pooling layer, a fusion layer, and a spatial-frequency convolutional layer; the multi-scale one-dimensional convolutional layer comprises multiple parallel one-dimensional convolutions at different scales; and the spatial-frequency convolutional layer comprises a frequency-domain one-dimensional convolution and a spatial-domain one-dimensional convolution that are successively connected in series;

input of the multi-scale one-dimensional convolutional layer is one piece of source domain data and target domain data, which are output to the concatenation layer;

the concatenation layer concatenates received multiple features at different scales to obtain a source-domain brainprint temporal-domain feature $Zt_{sj}$ and a target-domain brainprint temporal-domain feature $Zt_{tj}$,

TABLE 1

Accuracy rates (ACC) and Equal error rates (EER) of the model on a cross-session identification data set

| | Model | Classification-1 | | Classification-2 | | Average | |
|---|---|---|---|---|---|---|---|
| | | ACC | EER | ACC | EER | ACC | EER |
| Domain consolidation | EEGNet | 83.39 | 5.70 | 75.83 | 8.37 | 79.61 | 7.04 |
| | EEGNet-PSD | 80.90 | 5.04 | 82.06 | 5.04 | 81.48 | 5.04 |
| | CNN-RNN | 79.94 | 4.95 | 76.36 | 6.90 | 78.15 | 5.97 |
| | ix-vector | — | — | 86.40 | 5.02 | — | — |
| Multiple source domains | MEERNet | 76.11 | 6.25 | 81.37 | 4.55 | 78.74 | 5.40 |
| | MTDANN | 76.81 | 6.37 | 80.47 | 5.20 | 78.64 | 5.78 |
| | TFSAN (in the present disclosure) | 87.78 | 4.49 | 92.35 | 2.94 | 90.07 | 3.71 | wherein j∈[1, K], and then separately outputs the foregoing features to the maximum pooling layer and the fusion layer;

the maximum pooling layer performs dimensionality reduction processing on the received features in a time dimension, and outputs processed features to the TSFAN;

the TSFAN receives features output by the maximum pooling layer of the K specific-domain feature extraction networks, performs interaction processing on the features to obtain source-domain spatial-frequency attention $Q_{sj}$ and target-domain spatial-frequency attention $Q_{tj}$ that comprise an interaction correlation between the features, and then outputs the foregoing attention to the fusion layer, specifically:

the TSFAN implements, by using two fully connected layers, nonlinear mapping of the features output by the K specific-domain feature extraction networks, to obtain the source-domain spatial-frequency attention $Q_{sj}$ and the target-domain spatial-frequency attention $Q_{tj}$:

$$Q_{sj} = F_{bj}(Relu(F_{aj}(P_{sj}; V_j)); U_j) \quad \text{formula (1)}$$

and $$Q_{tj} = F_{bj}(Relu(F_{aj}(P_{tj}; V_j)); U_j),$$

wherein $F_{aj}$ and $F_{bj}$ represent two fully connected layers of $j^{th}$ source domain space, $V_i$ and $U_j$ represent parameters of the two fully connected layers, Relu(.) is an activation function, $P_{sj} \in \mathbb{R}^{c \times s}$ and $P_{tj} \in \mathbb{R}^{c \times s}$ represent a source-domain spatial-frequency feature and a target-domain spatial-frequency feature that are output by the maximum pooling layer, c is a quantity of EEG channels of a raw feature, and s is a frequency domain dimension size of the raw feature;

the fully connected layer parameter $U_j \in \mathbb{R}^{c's \times cs}$ in formula (1) is tensorized to a (K+1)-order higher-order tensor $\mathcal{W} \in \mathbb{R}^{c's \times c's \times \cdots \times cs}$, to obtain the interaction correlation between the features, wherein c' is a quantity of EEG channels of a feature obtained after being processed by the fully connected layer $F_{aj}$, and s' is a frequency domain dimension size of the feature obtained after being processed by the fully connected layer $F_{aj}$, and considering that a curse of dimensionality is caused as a quantity of source domains increases, a low-rank Tucker form is used to represent the (K+1)-order higher-order tensor $\mathcal{W}$:

$$\mathcal{W} = \mathcal{U} \times_1^2 W_1 \times_2^2 W_2 \times \ldots \times_{K+1}^2 W_{K+1}, \quad \text{formula (2)}$$

wherein $$\mathcal{U} \in \mathbb{R}^{r_1 \times \ldots \times r_{K+1}}, \{W_n \in \mathbb{R}^{r_n \times I_n}\}_{n=1}^{K+1}, \{r_1 \ldots r_{K+1}\}$$

is ranks in the Tucker form, $I_1 = I_2 = \ldots = I_K = c's'$, $I_{K+1} = cs$, c is a quantity of EEG channels of a raw feature, and s is a frequency domain dimension size of the raw feature;

the fusion layer respectively fuses the received source-domain brainprint temporal-domain feature $Zt_{sj}$ and the received target-domain brainprint temporal-domain feature $Zt_{tj}$ with the source-domain spatial-frequency attention $Q_{sj}$ and the target-domain spatial-frequency attention $Q_{tj}$, to obtain a source-domain brainprint temporal-domain feature $Zt'_{sj}$ and a target-domain brainprint temporal-domain feature $Zt'_{tj}$ that are spatial-frequency enhanced, and outputs the obtained features to the spatial-frequency convolutional layer; and the spatial-frequency convolutional layer extracts the received temporal-domain features $Zt'_{sj}$ and $Zt'_{tj}$ by using a frequency-domain one-dimensional convolution operation and a spatial-domain one-dimensional convolution operation, to obtain a source-domain temporal-spatial-frequency brainprint feature $Z_{sj}$ and a target-domain temporal-spatial-frequency brainprint feature $Z_{tj}$;

step (3): constructing a classifier used for brainprint recognition, and training and testing the classifier; and flattening the source-domain temporal-spatial-frequency brainprint feature $Z_{sj}$ and the target-domain temporal-spatial-frequency brainprint feature $Z_{tj}$ that are output in step (2), and calculating, by using the fully connected layer and a Softmax activation function, a probability that a sample belongs to each category; and step (4): recognizing an identity of an individual by implementing cross-session brainprint recognition using the domain adaptation network model based on tensorized spatial-frequency attention and the classifier used for brainprint recognition that are trained and tested.

2. The method according to claim 1, wherein filtering the raw EEG data by using the Butterworth filter in step 1-2 comprises: downsampling the EEG data to 250 Hz, and performing 0-75 Hz filtering processing on the raw EEG data by using the Butterworth filter.

3. The method according to claim 1, wherein performing STFT in step 1-2 comprises performing short-time Fourier transform (STFT) on a filtered signal x to extract a temporal-frequency feature, wherein a time-limited window function h(t) is used, it is assumed that a non-stationary signal x is stationary in one time window, a group of local "spectra" of the signal are obtained by performing segment-by-segment analysis on the signal x by moving the window function h(t) on a time axis, and STFT of a signal x(τ) is defined as:

$$STFT(t, f) = \int_{-\infty}^{\infty} x(\tau)h(\tau - t)e^{-j2\pi f \tau}d\tau, \quad \text{formula (3)}$$

wherein

STFT(t, f) represents STFT of the signal x(τ) at time t, h(τ–t) is a window function, and f represents a frequency.

4. The method according to claim 1, wherein the fusion layer is:

$$Zt'_{sj} = Zt_{sj} + Zt_{sj} \otimes \text{Sigmoid}(Q_{sj}) \quad \text{formula (4)}$$

and $$Zt'_{tj} = Zt_{tj} + Zt_{tj} \otimes \text{Sigmoid}(Q_{tj})$$

5. The method according to claim 1, wherein a loss function $\mathcal{L}_{cls}$ of the classifier used for brainprint recognition is:

$$\mathcal{L}_{cls} = E(\theta_f, \theta_y) = \sum\nolimits_{i=1,\ldots,N} \mathcal{L}_y^i(\theta_f, \theta_y), \quad \text{formula (5)}$$

$\theta_y$ is a classifier parameter, N is a quantity of categories, $\theta_f$ represents a feature extractor parameter, $\mathcal{L}_y^i(\theta_f, \theta_y)$ represents a cross-entropy loss of an $i^{th}$ type, and $E(\cdot)$ represents a cross-entropy function.

6. The method according to claim 5, wherein a total loss function $\mathcal{L}_{total}$ of the domain adaptation network model based on tensorized spatial-frequency attention and the classifier used for brainprint recognition is:

$$\mathcal{L}_{total} = \mathcal{L}_{cls} + \lambda \mathcal{L}_{dist} + \gamma \mathcal{L}_{disc}, \quad \text{formula (6)}$$

$\mathcal{L}_{disc}$ represents a loss function used to measure a distance of the classifier, $\mathcal{L}_{dist}$ represents a loss function used to measure a distribution difference between the source domain data and the target domain data, and $\lambda$ and $\gamma$ are super parameters.

7. A non-transitory computer-readable storage medium for cross-session brainprint recognition based on a tensorized spatial-frequency attention network (TSFAN) with domain adaptation, wherein a computer program is stored on the computer-readable storage medium, and when the computer program is executed in a computer, the computer is enabled to perform the following steps:

step (1): preprocessing raw electroencephalogram (EEG) data;

step 1-1: in a same experimental paradigm, acquiring EEG data generated by multiple subjects under external stimulation in different sessions;

step 1-2: filtering the raw EEG data by using a Butterworth filter, and then performing Short-time Fourier Transform (STFT);

step 1-3: intercepting EEG data processed in step 1-2, and labeling corresponding EEG sample data with a label of a subject; and step 1-4: classifying EEG sample data processed in step 1-3 into a training set and a test set in proportion, wherein training set data comprises data in K sessions, namely, K source domains, K≥2, and the test set serves as a target domain;

step (2): constructing a domain adaptation network model based on tensorized spatial-frequency attention, and training and testing the domain adaptation network model based on tensorized spatial-frequency attention wherein the domain adaptation network model based on tensorized spatial-frequency attention-comprises K specific-domain feature extraction networks with a same structure and one TSFAN; each specific-domain feature extraction network comprises a multi-scale one-dimensional convolutional layer, a concatenation layer, a maximum pooling layer, a fusion layer, and a spatial-frequency convolutional layer; the multi-scale one-dimensional convolutional layer comprises multiple parallel one-dimensional convolutions at different scales; and the spatial-frequency convolutional layer comprises a frequency-domain one-dimensional convolution and a spatial-domain one-dimensional convolution that are successively connected in series;

input of the multi-scale one-dimensional convolutional layer is one piece of source domain data and target domain data, which are output to the concatenation layer;

the concatenation layer concatenates received multiple features at different scales to obtain a source-domain brainprint temporal-domain feature $Zt_{sj}$ and a target-domain brainprint temporal-domain feature $Z_{tj}$, wherein j∈[1, K], and then separately outputs the foregoing features to the maximum pooling layer and the fusion layer;

the maximum pooling layer performs dimensionality reduction processing on the received features in a time dimension, and outputs processed features to the TSFAN;

the TSFAN receives features output by the maximum pooling layer of the K specific-domain feature extraction networks, performs interaction processing on the features to obtain source-domain spatial-frequency attention $Q_{sj}$ and target-domain spatial-frequency attention $Q_{tj}$ that comprise an interaction correlation between the features, and then outputs the foregoing attention to the fusion layer, specifically;

the TSFAN implements, by using two fully connected layers, nonlinear mapping of the features output by the K specific-domain feature extraction networks, to obtain the source-domain spatial-frequency attention $Q_{sj}$ and the target-domain spatial-frequency attention $Q_{tj}$;

$$Q_{sj} = F_{bj}(Relu(F_{aj}(P_{sj}; V_i)); U_j) \text{ and,} \quad \text{formula (1)}$$

$$Q_{tj} = F_{bj}(Relu(F_{aj}(P_{tj}; V_i)); U_j)$$

wherein $F_{aj}$ and $F_{bj}$ represent two fully connected layers of $i^{th}$ source domain space, $V_j$ and $U_j$ represent parameters of the two fully connected layers, Relu(.) is an activation function, $P_{sj} \in \mathbb{R}^{c \times s}$ and $P_{tj} \in \mathbb{R}^{c \times s}$ represent a source-domain spatial-frequency feature and a target-domain spatial-frequency feature that are output by the maximum pooling layer, c is a quantity of EEG channels of a raw feature, and s is a frequency domain dimension size of the raw feature;

the fully connected layer parameter $U_j \in \mathbb{R}^{c's \times cs}$ in formula (1) is tensorized to a (K+1)-order higher-order tensor $\mathcal{W} \in \mathbb{R}^{c's \times c's \times \cdots \times cs}$, to obtain the interaction correlation between the features, wherein c' is a quantity of EEG channels of a feature obtained after being processed by the fully connected layer $F_{aj}$, and s' is a frequency domain dimension size of the feature obtained after being processed by the fully connected layer $F_{aj}$, and considering that a curse of dimensionality is caused as a quantity of source domains increases, a low-rank Tucker form is used to represent the (K+1)-order higher-order tensor $\mathcal{W}$:

$$\mathcal{W} = \mathcal{U} \times_1^2 W_1 \times_2^2 W_2 \times \ldots \times_{K+1}^2 W_{K+1}, \quad \text{formula (2)}$$

wherein $$\mathcal{U} \in \mathbb{R}^{r_1 \times \cdots \times r_{K+1}}, \{W_n \in \mathbb{R}^{r_n \times I_n}\}_{n=1}^{K+1} [\![r]\!]_1 \cdots r_{K+1}\}$$

is ranks in the Tucker form, $I_1 = I_2 = \ldots = I_K = c's'$, $I_{K+1} = cs$, c is a quantity of EEG channels of a raw feature, and s is a frequency domain dimension size of the raw feature;

the fusion layer respectively fuses the received source-domain brainprint temporal-domain feature $Zt_{sj}$ and the received target-domain brainprint temporal-domain feature $Z_{tj}$ with the source-domain spatial-frequency attention $Q_{sj}$ and the target-domain spatial-frequency attention $Q_{tj}$, to obtain a source-domain brainprint temporal-domain feature $Zt'_{sj}$ and a target-domain brainprint temporal-domain feature $Zt'_{tj}$ that are spatial-frequency enhanced, and outputs the obtained features to the spatial-frequency convolutional layer; and the spatial-frequency convolutional layer extracts the received temporal-domain features $Zt'_{sj}$ and $Zt'_{tj}$ by using a frequency-domain one-dimensional convolution operation and a spatial-domain one-dimensional convolution operation, to obtain a source-domain temporal-spatial-frequency brainprint feature $Z_{sj}$ and a target-domain temporal-spatial-frequency brainprint feature $Z_{tj}$;

step (3): constructing a classifier used for brainprint recognition, and training and testing the classifier; and flattening the source-domain temporal-spatial-frequency brainprint feature $Z_{sj}$ and the target-domain temporal-spatial-frequency brainprint feature $Z_{tj}$ that are output in step (2), and calculating, by using the fully connected layer and a Softmax activation function, a probability that a sample belongs to each category; and step (4): recognizing an identity of an individual by implementing cross-session brainprint recognition by using the domain adaptation network model based on tensorized spatial-frequency attention and the classifier used for brainprint recognition that are trained and tested.

8. The non-transitory computer-readable storage medium according to claim 7, wherein filtering the raw EEG data by using the Butterworth filter in step 1-2 comprises: downsampling the EEG data to 250 Hz, and performing 0-75 Hz filtering processing on the raw EEG data by using the Butterworth filter.

9. The non-transitory computer-readable storage medium according to claim 7, wherein performing STFT in step 1-2 comprises: performing short-time Fourier transform (STFT) on a filtered signal x to extract a temporal-frequency feature, wherein a time-limited window function h(t) is used, it is assumed that a non-stationary signal x is stationary in one time window, a group of local "spectra" of the signal are obtained by performing segment-by-segment analysis on the signal x by moving the window function h(t) on a time axis, and STFT of a signal $x(\tau)$ is defined as:

$$STFT(t, f) = \int_{-\infty}^{\infty} x(\tau)h(\tau - t)e^{-j2\pi f\tau}d\tau, \quad \text{formula (3)}$$

wherein

STFT(t, f) represents STFT of the signal $x(\tau)$ at time t, $h(\tau-t)$ is a window function, and f represents a frequency.

10. The non-transitory computer-readable storage medium according to claim 7, wherein the fusion layer is:

$$Zt'_{sj} = Zt_{sj} + Zt_{sj} \otimes \text{Sigmoid}(Q_{sj}) \quad \text{formula (4)}$$

and $$Zt'_{tj} = Zt_{tj} + Zt_{tj} \otimes \text{Sigmoid}(Q_{tj})$$

11. The non-transitory computer-readable storage medium according to claim 7, wherein a loss function $\mathcal{L}_{cls}$ of the classifier used for brainprint recognition is:

$$\mathcal{L}_{cls} = E(\theta_f, \theta_y) = \sum_{i=1,\ldots,N} \mathcal{L}_y^i(\theta_f, \theta_y), \quad \text{formula (5)}$$

wherein $\theta_y$ is a classifier parameter, N is a quantity of categories, $\theta_f$ represents a feature extractor parameter, $\mathcal{L}_y^i(\theta_f, \theta_y)$ represents a cross-entropy loss of an $i^{th}$ type, and E(•) represents a cross-entropy function.

12. The non-transitory computer-readable storage medium according to claim 11, wherein a total loss function $\mathcal{L}_{total}$ of the domain adaptation network model based on tensorized spatial-frequency attention and the classifier used for brainprint recognition is:

$$\mathcal{L}_{total} = \mathcal{L}_{cls} + \lambda \mathcal{L}_{dist} + \gamma \mathcal{L}_{disc}, \quad \text{formula (6)}$$

wherein $\mathcal{L}_{disc}$ represents a loss function used to measure a distance of the classifier, $\mathcal{L}_{dist}$ represents a loss function used to measure a distribution difference between the source domain data and the target domain data, and $\lambda$ and $\gamma$ are super parameters.

13. A computing device for cross-session brainprint recognition based on a tensorized spatial-frequency attention network (TSFAN) with domain adaptation, comprising a memory and a processor, wherein the memory stores executable code, and when executing the executable code, the processor implements the following steps:

step (1): preprocessing raw electroencephalogram (EEG) data;

step 1-1: in a same experimental paradigm, acquiring EEG data generated by multiple subjects under external stimulation in different sessions;

step 1-2: filtering the raw EEG data by using a Butterworth filter, and then performing Short-time Fourier Transform (STFT);

step 1-3: intercepting EEG data processed in step 1-2, and labeling corresponding EEG sample data with a label of a subject; and step 1-4: classifying EEG sample data processed in step 1-3 into a training set and a test set in proportion, wherein training set data comprises data in K sessions, namely, K source domains, K≥2, and the test set serves as a target domain;

step (2): constructing a domain adaptation network model based on tensorized spatial-frequency attention, and training and testing the domain adaptation network model based on tensorized spatial-frequency attention wherein the domain adaptation network model based on tensorized spatial-frequency attention-comprises K specific-domain feature extraction networks with a same structure and one TSFAN; each specific-domain feature extraction network comprises a multi-scale one-dimensional convolutional layer, a concatenation layer, a maximum pooling layer, a fusion layer, and a spatial-frequency convolutional layer; the multi-scale one-dimensional convolutional layer comprises multiple parallel one-dimensional convolutions at different scales; and the spatial-frequency convolutional layer comprises a frequency-domain one-dimensional convolution and a spatial-domain one-dimensional convolution that are successively connected in series;

input of the multi-scale one-dimensional convolutional layer is one piece of source domain data and target domain data, which are output to the concatenation layer;

the concatenation layer concatenates received multiple features at different scales to obtain a source-domain brainprint temporal-domain feature $Zt_{sj}$ and a target-domain brainprint temporal-domain feature $Z_{tj}$, wherein $j \in [1, K]$, and then separately outputs the foregoing features to the maximum pooling layer and the fusion layer;

the maximum pooling layer performs dimensionality reduction processing on the received features in a time dimension, and outputs processed features to the TSFAN;

the TSFAN receives features output by the maximum pooling layer of the K specific-domain feature extraction networks, performs interaction processing on the features to obtain source-domain spatial-frequency attention $Q_{sj}$ and target-domain spatial-frequency attention $Q_{tj}$ that comprise an interaction correlation between the features, and then outputs the foregoing attention to the fusion layer, specifically:

the TSFAN implements, by using two fully connected layers, nonlinear mapping of the features output by the K specific-domain feature extraction networks, to obtain the source-domain spatial-frequency attention $Q_{sj}$ and the target-domain spatial-frequency attention $Q_{tj}$;

$$Q_{sj} = F_{bj}(Relu(F_{aj}(P_{sj}; V_i)); U_j) \text{ and,}$$
$$Q_{tj} = F_{bj}(Relu(F_{aj}(P_{tj}; V_i)); U_j) \quad \text{formula (1)}$$

wherein $F_{aj}$ and $F_{bj}$ represent two fully connected layers of $j^{th}$ source domain space, $V_i$ and $U_j$ represent parameters of the two fully connected layers, Relu(.) is an activation function, $P_{sj} \in \mathbb{R}^{c \times s}$ and $P_{sj} \in \mathbb{R}^{c \times s}$ represent a source-domain spatial-frequency feature and a target-domain spatial-frequency feature that are output by the maximum pooling layer, c is a quantity of EEG channels of a raw feature, and s is a frequency domain dimension size of the raw feature;

the fully connected layer parameter $U_j \in \mathbb{R}^{c's \times cs}$ in formula (1) is tensorized to a (K+1)-order higher-order tensor $\mathcal{W} \in \mathbb{R}^{c's \times c's \times \cdots \times cs}$, to obtain the interaction correlation between the features, wherein c' is a quantity of EEG channels of a feature obtained after being processed by the fully connected layer $F_{aj}$, and s' is a frequency domain dimension size of the feature obtained after being processed by the fully connected layer $F_{aj}$, and considering that a curse of dimensionality is caused as a quantity of source domains increases, a low-rank Tucker form is used to represent the (K+1)-order higher-order tensor $\mathcal{W}$:

$$\mathcal{W} = \mathcal{U} \times_1^2 W_1 \times_2^2 W_2 \times \ldots \times_{K+1}^2 W_{K+1}, \quad \text{formula (2)}$$

wherein $$\mathcal{U} \in \mathbb{R}^{r_1 \times \cdots \times r_{K+1}}, \{W_n \in \mathbb{R}^{r_n \times I_n}\}_{n=1}^{K+1} [\{r\}_1 \ldots r_{K+1}\}$$

is ranks in the Tucker form, $I_1 = I_2 = \ldots = _K = c's'$, $I_{K+1} = cs$, c is a quantity of EEG channels of a raw feature, and s is a frequency . . . domain dimension size of the raw feature;

the fusion layer respectively fuses the received source-domain brainprint temporal-domain feature $Zt_{sj}$ and the received target-domain brainprint temporal-domain feature $Zt_{tj}$ with the source-domain spatial-frequency attention $Q_{sj}$ and the target-domain spatial-frequency attention $Q_{tj}$, to obtain a source-domain brainprint temporal-domain feature $Zt'_{sj}$ and a target-domain brainprint temporal-domain feature $Zt'_{tj}$ that are spatial-frequency enhanced, and outputs the obtained features to the spatial-frequency convolutional layer; and the spatial-frequency convolutional layer extracts the received temporal-domain features $Zt'_{sj}$ and $Zt'_{tj}$ by using a frequency-domain one-dimensional convolution operation and a spatial-domain one-dimensional convolution operation, to obtain a source-domain temporal-spatial-frequency brainprint feature $Z_{sj}$ and a target-domain temporal-spatial-frequency brainprint feature $Z_{tj}$;

step (3): constructing a classifier used for brainprint recognition, and training and testing the classifier; and flattening the source-domain temporal-spatial-frequency brainprint feature $Z_{sj}$ and the target-domain temporal-spatial-frequency brainprint feature $Z_{tj}$ that are output in step (2), and calculating, by using the fully connected layer and a Softmax activation function, a probability that a sample belongs to each category; and step (4): recognizing an identity of an individual by implementing cross-session brainprint recognition using the domain adaptation network model based on tensorized spatial-frequency attention and the classifier used for brainprint recognition that are trained and tested.

14. The computing device according to claim 13, wherein filtering the raw EEG data by using the Butterworth filter in step 1-2 comprises: downsampling the EEG data to 250 Hz, and performing 0-75 Hz filtering processing on the raw EEG data by using the Butterworth filter.

* * * * *